United States Patent [19]

Khan et al.

[11] Patent Number: 5,439,681
[45] Date of Patent: Aug. 8, 1995

[54] PARACHLOROMETAXYLENOL ANTIMICROBIAL FORMULATION

[75] Inventors: Mohammad A. Khan, Sandy; Minh Q. Hoang, Taylorsville, both of Utah

[73] Assignee: Becton Dickinson and Company, Franklin Lakes, N.J.

[21] Appl. No.: 72,658

[22] Filed: Jun. 7, 1993

Related U.S. Application Data

[63] Continuation of Ser. No. 675,362, Mar. 25, 1991.

[51] Int. Cl.$^6$ .................. A01N 25/02; A01N 25/30; A61K 9/08
[52] U.S. Cl. ............................. 424/400; 424/405
[58] Field of Search ............................. 424/400, 405

[56] References Cited

U.S. PATENT DOCUMENTS

| | | |
|---|---|---|
| 3,326,808 | 6/1967 | Noseworthy ................. 252/106 |
| 3,960,745 | 6/1976 | Billany et al. ................ 252/106 |
| 4,157,977 | 6/1979 | Dewar et al. ................. 252/106 |
| 4,252,665 | 2/1981 | Casey et al. ................. 252/106 |
| 4,257,907 | 3/1981 | Langguth et al. ............ 252/106 |
| 4,326,977 | 4/1982 | Schmolka .................... 252/106 |
| 4,456,543 | 6/1984 | Owens ......................... 252/106 |
| 4,632,772 | 12/1986 | Garabedian et al. ......... 252/106 |

FOREIGN PATENT DOCUMENTS 0223681 10/1986 European Pat. Off. .
2203339 4/1988 United Kingdom .

OTHER PUBLICATIONS

"Topical Antimicrobial Products", 72,032 Food Drug Cosmetic Law Reports.

The Merck Index: An Encyclopedia of Chemicals and Drugs, ed 9., Rahway, New Jersey, Merck and Co., 1976.

Ray et al., "Microbiological Evaluation of PCMX Complexes." *J. Pharmacol Sci.* 57:609-613 (1968).

*Primary Examiner*—Edward J. Webman
*Attorney, Agent, or Firm*—Nanette S. Thomas; Bruce S. Weintraub

[57] ABSTRACT

A unique antimicrobial composition comprising parachlorometaxylenol, nonionic surfactant, anionic surfactant, foam builder, moisturizer and/or emollient thickener and an acid to adjust to pH. The composition is useful in providing antimicrobial effectiveness in surgical scrub applications with mildness characteristics.

1 Claim, No Drawings

PARACHLOROMETAXYLENOL ANTIMICROBIAL FORMULATION

This is continuing application of Ser. No. 07/675,362 filed on Mar. 25, 1991.

BACKGROUND OF THE INVENTION

1. Field of the Invention

This invention relates to antimicrobial formulations for providing antimicrobial effectiveness to the skin without irritation or dryness. The formulations, comprising parachlorometaxylenol, are particularly useful in the health care profession such as in surgical practice as a pre-operative scrub.

2. Description of Related Art

Effective antiseptic or disinfectant compositions can be formed by combining a surfactant or detergent with an antimicrobial agent. Thus, antiseptic cleaning compounds can be formulated rather easily; however, many such compositions are not suitable for use in contact with human skin due to the abrasive nature of the surfactant-containing composition, and there are surfactants incompatible with many antimicrobial agents.

Where the composition is intended for use as surgical scrub, mildness is an important consideration. Mildness indicates the composition does not cause excessive irritation of the skin, such as erythema.

In a majority of cases, skin irritation can be attributed to contact of the skin with a surfactant. It is believed that skin irritation results partly due to the nature of the surfactant itself and, in part, due to the action of the surfactant in weakening the resistance of the skin. The degree of irritation may vary significantly with the surfactant, the individual user, the length of contact and the conditions of contact. In many cases the degree of irritation is also affected by the combination of the antimicrobial agent and the surfactant.

It is believed that surfactants have a denaturing effect on the skin. Thus, antimicrobial agents or chemicals which normally do not irritate the skin when combined with a surfactant can penetrate or be readily absorbed by the skin and cause irritation. The absorption of antimicrobial agents or chemicals by the skin is generally undesirable.

Surgical scrub procedures and techniques are highly conducive to the development of erythema and other irritations. All personnel involved in surgical procedures use a surgical scrub in preparation for surgery. Frequently, the same individual will scrub three to five times on a single day. A typical surgical scrub involves placing a cleansing composition on the hand. Commonly, a brush or sponge is used and the arms from the elbows to the fingertips are scrubbed thoroughly for as long as ten minutes. Thus, the epidermal layers of the skin are subject to significant rubbing and aggravation. After the arms and hands have been scrubbed they are rinsed, dried and placed into rubber gloves. The rinse is often not complete and residual surfactant and/or antimicrobial compounds from the cleansing composition are left on the skin. Many times, the hands remain gloved for as long as six hours. During this time the hand perspires and the pores can open and enlarge, thereby allowing residual surfactants and/or antimicrobial compounds to penetrate the skin. This in turn can create topical skin irritations. The likelihood of irritation or erythema increases with the frequency one performs the surgical scrub procedure. It is important that surgical scrub compositions be very mild, but yet effective.

Numerous attempts have been made to develop formulations containing antimicrobial agents and surfactants, which reduce or eliminate skin irritation and provide effective antiseptic or disinfectant properties. However, the efficacy of antiseptic or disinfectant compositions is greatly influenced by a number of variables, including pH, temperature, concentration of organisms, duration of exposure, concentration of the antiseptic and the type of surfactants used in the formulation.

Formulations containing the antimicrobial agent, chlorhexidine, have been used as antibacterial skin cleaners in surgical scrubs. Formulations containing chlorhexidine generally include a surfactant and a low percentage of an alcohol such as isopropanol.

Billany et al., U.S. Pat. No. 3,960,745, discloses a chlorhexidine cleansing composition formulated with a polyoxyethylene-polyoxypropylene nonionic surfactant. The formulation is commercially available as HIBICLENS ® (trademark of ICI Americas, Inc.) sold by Stuart Pharmaceuticals, Wilmington, Del. Billany et al. discloses that anionic surfactants are not desirable surfactants because they may destroy the antibacterial activity of chlorhexidine solutions by complexing with the cationic chlorhexidine. Cationic surfactants are also not desirable because of their irritancy, and because, in combination with a soluble chlorhexidine salt, double decomposition can occur with the formation of insoluble chlorhexidine salts and consequent loss of antibacterial activity. Equally unsuitable surfactants for use in such formulations are amphoteric surfactants, which contain either anionic or cationic centers, depending upon pH, and they suffer from the above-described disadvantages of anionic and cationic surfactants.

Other formulations have used bisbiguanide as an antimicrobial agent as disclosed in U.S. Pat. No. 4,456,543 to Ownes. Ownes discloses an antibacterial cleansing formulation containing bisbiguanide and one or more nonionic polyoxyalkylene surfactants.

Dewar et al., U.S. Pat. No. 4,157,977 discloses surfactant-germicide compositions containing an antimicrobial active phenolic derivative in combination with hydroxyacetic acid and a surfactant.

Casey et al., U.S. Pat. No. 4,252,665 discloses a disinfectant cleaning composition containing ortho-benzyl-para-chlorophenol, anionic surfactants and sulfobetaine surfactants.

Langguth et al., U.S. Pat. No. 4,257,907 discloses disinfectant cleaning compositions containing ortho-benzyl-para-chlorophenol, sulfobetaine surfactants and anionic surfactants.

White, European Patent Application 0 223 681, discloses an alcohol-based antimicrobial composition.

Meldovanyl et al., United Kingdom Application 2 203 339, discloses a microbicidal formulation containing antimicrobial agents and surfactants.

Formulations containing the antimicrobial agent parachlorometaxylenol (PCMX) have been developed as disclosed in U.S. Pat. No. 4,632,772 to Garabedian et al. Garabedian et al. discloses an antimicrobial composition containing the active antimicrobial agent PCMX and an ionic surfactant, alkyl aryl ethoxylated sulfonate.

Melvin, U.S. Pat. No. 3,326,808 discloses an antiseptic surfactant composition containing PCMX and an anionic surfactant, the sodium salt of 2-sulfomethyl myristate.

PCMX, being phenolic in nature with acidic hydrogen and insoluble in water, reacts with bases to form salts:

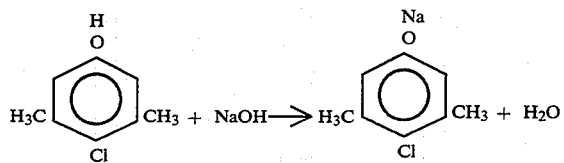

PCMX exists in the salt form in solutions at higher pH and in the phenolic state at lower pH. Therefore, efficacy of the PCMX formulation is greatly influenced by pH. The efficacy of PCMX is also compromised by other factors such as solubility and the formation of an association complex with other components in a formulation.

PCMX is related to other phenolic compounds such as cresol, carbolic acid, and hexachlorophene and has a characteristic phenolic odor. Other names for PCMX include chloroxylenol; 4-chloro-3, 5-xylenol; 4-chloro-3,5-dimethylphenol, 2-chloro-m-xylenol; 2-chloro-5-hydroxy-m-xylene; 2-5-hydroxy-m-xylene; 2-chloro-5-hydroxy-1,3-dimethylbenzene; 4-chlor-1-hydroxy-3, 5-dimethyl benzene; and 3,5-dimethyl-4-chlorophenol.

PCMX is a desirable antimicrobial agent having sixty times the antimicrobial activity of other phenolics against a variety of gram-positive and gram-negative bacteria as reported by Windholz, M(ed). *The Merck Index: An Encyclopedia of Chemicals and Drugs*, ed 9. Rahway, N.J., Merck and Co., 1976. However, as reported by Ray et al., "Microbiological Evaluation of PCMX Complexes." *J. Pharmacol Sci.* 57:609–613 (1968), PCMX will react with various nonionic macromolecules such as polyethylene glycol, methyl-cellulose and polysorbate to form association complexes and therefore diminish the inhibiting and bactericidal activity of PCMX.

Furthermore, as disclosed in U.S. Pat. No. 4,326,977 to Schmolka, the efficacy of antiseptic compositions may be influenced by the type of surfactants used because some surfactants are incompatible with many antiseptic agents.

Therefore, due to the antimicrobial activity of PCMX, it is desirable to have a PCMX formulation which provides substantially maximized efficacy and does not promote dryness or irritation to the skin. However, such a formulation is difficult to produce due to the incompatibility of many surfactants with many antiseptic agents like PCMX.

SUMMARY OF THE INVENTION

The present invention is an antimicrobial composition comprising an antimicrobial agent and effective surfactants. The composition may be effectively used as a surgical scrub without irritation or dryness to skin.

The antimicrobial composition desirably comprises an active antimicrobial agent, surfactants, a foam builder, moisturizers and/or emollients, a thickener and water.

The antimicrobial composition preferably comprises an active antimicrobial agent, a nonionic surfactant, an anionic surfactant, a foam builder, moisturizers and/or emollients, a thickener and water.

An effective antimicrobial composition preferably comprises the active ingredients comprising para-chlorometaxylenol (PCMX), a specific nonionic surfactant and a specific anionic surfactant in specific amounts so that PCMX will solubilize completely and will not complex with the surfactants.

Most preferably, the antimicrobial composition comprises:
 (a) from about 0.5% to about 3.75% of para-chlorometaxylenol (PCMX);
 (b) from about 1.0% to about 6.0% of a nonionic surfactant;
 (c) from about 2.0% to about 12.0% of an anionic surfactant;
 (d) from about 5.0% to about 15.0% of moisturizers and/or emollients;
 (e) from about 2.0% to about 12.0% of a foam builder;
 (f) from about 0.1% to about 1.0% of a thickener;
 (g) from about 0.05% to about 0.5% of a fragrance;
 (h) from about 60.0% to about 85.0% of water;
 (i) from about 0.0% to about 1.0% of EDTA; and
 (k) a sufficient amount of acid if necessary to adjust the pH to about 4.5.

Antimicrobial compositions of the present invention are useful in providing substantial antimicrobial effectiveness and substantial non-irritancy to the skin.

Another attribute of the antimicrobial compositions is their ability not to dry the skin.

A most significant advantage of the antimicrobial compositions is their use in the health care profession as effective surgical scrubs.

An advantage of the antimicrobial compositions is that they provide substantial bactericidal effectiveness. In particular, they provide bactericidal effectiveness with respect to *Staphylococcus aureus, Candida albicans, Pseudomonas aeruginosa, Escherichia coli* and the like.

Further advantages of the antimicrobial compositions of the present invention is their significant foaming properties, good solubility in water and adequate detergency.

A further advantage of the antimicrobial compositions is that the components do not readily penetrate or are not readily absorbed by the skin.

An advantage of the antimicrobial composition comprising the antimicrobial agent PCMX, an anionic surfactant and a nonionic surfactant is a unique cidal PCMX formulation. The combination of a particular anionic surfactant and a particular nonionic surfactant, in proper proportion will solubilize PCMX completely and will not form an association complex. The composition provides substantial antimicrobial effectiveness and substantial non-irritancy to the skin.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The antimicrobial composition preferably comprises:
 (a) an antimicrobial agent;
 (b) a nonionic surfactant;
 (c) an anionic surfactant;
 (d) a foam builder;
 (e) moisturizers and emollients;
 (f) a thickener (g) an acid; and
(h) water.

An antimicrobial agent is a compound or substance that kills microorganisms or prevents or inhibits their growth and reproduction.

The antimicrobial agent present in the antimicrobial composition is selected to combat the microorganism(s) of concern to the degree desired. The antimicrobial agent is selected so as not to upset desirable physical and chemical properties of human skin. A properly selected antimicrobial agent maintains stability under use and storage conditions (pH, temperature, light, etc.), for a required length of time. A desirable property of the antimicrobial agent is that it is safe and nontoxic in handling, formulation and use, is environmentally acceptable and cost effective.

The antimicrobial agent present in the antimicrobial composition must be capable of being solubilized in the composition without forming an association complex with other components of the composition. The formation of an association complex will prevent the antimicrobial composition from providing maximum antimicrobial efficacy.

Classes of antimicrobial agents include, but are not limited to, phenolics, halogen compounds, quarternary ammonium compounds, metal derivatives, amines, alkanolamines and nitro derivatives, anilides, organosulfur and sulfur-nitrogen compounds.

The preferred active antimicrobial agent in the antimicrobial composition is parachlorometaxylenol (PCMX). The efficacy of PCMX is greatly influenced by pH. PCMX melts at about 115° C. and boils at about 245° C. It is soluble in alcohol, ether, benzene, fixed oils, terpenes, and solutions of alkali hydroxides and is volatile with steam. Preferably, PCMX is present in the antimicrobial composition in an amount from about 1.5% to about 3.5%, and preferably at about 3.2%.

A surfactant is a surface-active agent or an organic substance with certain characteristic features in structure and property. The term surfactant is interchangeably used with detergent.

Surfactants are typically characterized by amphipathic structure, solubility, adsorption at interfaces, orientation of interfaces, micelle formation and functional properties.

A surfactant's classification as anionic, cationic, nonionic or amphoteric, depends on the charge of the surface-active moiety, usually the larger part of the molecule. An anionic surfactant carries a negative charge, a cationic surfactant carries a positive charge, a nonionic surfactant has no charge and an amphoteric surfactant has positive and negative charges in the molecule.

A specific selection of surfactants is required for the antimicrobial composition so that the antimicrobial agent is solubilized and an association complex is not formed between the antimicrobial agent and the surfactants. In particular, it is believed that cationic surfactants will associate to complex an antimicrobial agent such as PCMX and therefore adversely effect the antimicrobial efficacy of the antimicrobial composition.

It is believed that a combination of specific nonionic and anionic surfactants in the antimicrobial composition will completely solubilize the antimicrobial agent such as PCMX. The specific combination of nonionic and anionic surfactants will also not form an association complex with the antimicrobial agent such as PCMX.

A nonionic surfactant for the antimicrobial composition includes, but is not limited to, members of the class of block polymers that may be generically classified as poly(oxypropylene)poly-(oxyethylene) condensates whose various grades fall into a molecular weight range between 1000 to over 15,000, alkylphenol ethoxylates and primary alcohol ethoxylates.

A series of closely related suitable block polymers for the antimicrobial composition includes, but is not limited to PLURONIC® polyols (trademark of BASF, Wyandotte Corp., Wyandotte, Mich.). PLURONIC polyol is a polyglycol (polyoxypropylene-polyoxyethylene block copolymer; CAS registry no.: 9003-11-6). Particular PLURONIC potyols that are useful include, but are not limited to: L31, L35, F38, L43, L42, L62, L63, L64, P65, F68, L72, P75, F77, P84, P85, F87 and F88.

A desirable PLURONIC polyol in the antimicrobial composition is L64. PLURONIC polyol L64 limits the formation of an association complex between the surfactants and the antimicrobial agent in the composition. The approximate molecular weight of PLURONIC polyol L64 is 2900.

Preferably, the nonionic surfactant is present in the antimicrobial composition in an amount from about 1.0% to about 6.0% and preferably about 3.0% weight percent.

It is believed that the appropriate effective amount of nonionic surfactant in the antimicrobial composition is important because the nonionic surfactant is capable of stabilizing and solubilizing PCMX in solution so as to enhance and maximize the antimicrobial activity of the antimicrobial composition. If the appropriate effective amount of nonionic surfactant is not used, the antimicrobial properties of PCMX may be weakened.

A suitable anionic surfactant for the antimicrobial composition includes but is not limited to sulfated alkyl phenol ethoxylates and alkyl-aryl sulfonates. It is believed that only specific suitable anionic surfactants may be used with a specific nonionic surfactants so as to enhance and maximize the antimicrobial activity of the antimicrobial agent, such as PCMX.

A suitable anionic surfactant for the antimicrobial composition is GAFAC® LO-529 (trademark of GAF, Wayne, N.J.) sold by GAF which is a polyoxyethylene nonylphenol ether phosphate sodium salt.

Another suitable anionic surfactant for the antimicrobial composition is WITCONATE® P-1059 (trademark of WITCO) which is an alkyl-aryl sulfonate, isopropylamine salt.

A preferred anionic surfactant for the antimicrobial composition is ALIPAL® CO-436 (trademark of GAF, Wayne, N.J.) sold by GAF, which is an ammonium salt of sulfated nonylphenoxypoly(ethyleneoxy)ethanol (poly(oxy-1,2-ethandyl.

Preferably, the anionic surfactant is present in the antimicrobial composition in an amount from about 2.0% to about 12.0% and preferably at about 8.0%. The anionic surfactant should preferably be used in the antimicrobial composition in an amount sufficient to maintain detergent action and so as not to adversely effect the active antimicrobial properties of the antimicrobial composition. In particular, it is not desirable for the anionic surfactant to complex with the antimicrobial agent.

A foam builder enhances the formability of the surfactants in the formulation. A desirable foam builder for the antimicrobial composition includes, but is not limited to ammonium fatty sulfosuccinate, alkanolamides such as cocodieth anolamide and amine oxides such as cetyldimethyl amino oxide.

A preferred foam builder for the antimicrobial composition is an ammonium lauryl sulfosuccinate, MONAMATE® LNT-40 (a trademark of MONA Industries, Paterson, N.J.) sold by MONA.

Preferably, the foam builder is present in the antimicrobial composition in an amount from about 2.0% to about 12.0% and most preferred at about 8.0%.

Emollients in their physical form are thin liquids, oils of various viscosities, fatty solids or waxes. Hydrocarbons function essentially as emollients by virtue of their ability to lubricate and/or hold water at the skin surface due to their relative occlusivity. Mineral oil is such a fluid. Some emollients are hydrophilic (glycerin, propylene glycol) and are water soluble lubricants and humectants. Since emollients may be fatty chemicals, oily or waxy in nature, they can impart barrier properties to formulations and are then referred to as moisturizers.

Moisturizers are substances which provide external lubricant behavior, such as to soften and sooth the skin because they encourage skin water retention.

The function of the moisturizer and/or emollient in the antimicrobial composition is to replace the natural skin oils which are lost or at least, partially removed by the cleansing action of the surfactants in the antimicrobial composition. Therefore chapping of the skin may be prevented. In addition, they also function to dissolve and maintain the oil-soluble antiseptics in the emulsion.

Suitable moisturizes and/or emollients in the antimicrobial composition include, but are not limited to lanolin, derivatives of lanolin such as the ethoxylated, acetylated alcohol and surface active alcohol derivatives of lanolin, propylene glycol, polypropylene glycol, polyethylene glycol, mineral oils, fatty alcohols and glycerine.

A preferable moisturizer and/or emollient for the antimicrobial composition is an ethoxylated (75 moles) lanolin, SOLULAN® 75 (trademark of Amerchol Corporation, Edison, N.J.) sold by Amerchol Corporation.

Another preferred moisturizer and/or emollient for the antimicrobial composition is an emollient extracted from aloe or an ester comprising isopropyl palmitate and lanolin oil, ISOPROPYLAN® 50 (trademark of Amerchol Corporation, Edison, N.J.) sold by Amerchol Corporation.

Another preferred moisturizer and/or emollient for the antimicrobial composition is a polyethyl glycol lanolin derivative, PEG® 75 lanolin (trademark of Amerchol Corporation, Edison, N.J.) sold by Amerchol Corporation.

Preferably, a combination of moisturizers and/or emollients is present in the antimicrobial composition in an amount from about 5.0% to about 15.0% and most preferred at about 11.2%.

A thickener is an additive. that increases the viscosity and stability of a formulation. A desirable thickener originates from cellulosic materials such as starch, methocel (methyl cellulose ethers) and hydroxyethyl cellulose. Other thickeners include high molecular weight pluronic surfactants and acrylics such as carbopol polymers.

It is believed that a more hydrophobic thickener provides a clear composition and improves activity of the composition because it uses a minimum amount of water from the composition to provide the thickening activity. Therefore, there is sufficient water in the composition to act as a solubilizing agent for other ingredients in the composition. A less hydrophilic thickener may cause the antimicrobial composition to be turbid or milky because the antimicrobial agent may precipitate if there is not sufficient water in the composition.

A preferred thickener for the antimicrobial composition is a cellulose, 2-hydroxyethyl ether, CELLUSIZE® (trademark of Union Carbide, Danbury, Conn.) sold by Union Carbide.

A most preferred thickener for the antimicrobial composition is METHOCEL® 40-100 (a trademark of Dow Chemical, U.S.A., Midland, Mich.) sold by Dow Chemical. METHOCEL thickener is 91% hydroxypropyl methyl-cellulose which dissolves in water, is nonionic and is a highly efficient water retention agent.

Preferably, the thickener is present in the antimicrobial composition in an amount from about 0.1% to about 1.0% and most preferred at about 0.5%.

Because the antimicrobial composition is greatly influenced by pH, small amounts, less than about 1.0%, of a nontoxic acidic substance may be added so as to maintain an effective level. Adjustment of the pH is desirable so the composition is compatible with the pH of skin and to avoid unnecessary irritation to the skin.

Suitable acids include hydrochloric acid, sulfuric acid, phosphoric acid, citric acid, lactic acid, and gluconic acid.

The antimicrobial formulation may be adjusted to a pH within the range from about 4.0% to about 6.0%. Most preferably the pH is within in the range of about 4.0% to about 5.0%.

The balance of the antimicrobial composition is preferably water. The water may be present in the antimicrobial composition in an amount from about 60.0% to about 85.0%.

Other ingredients which are conventional or desirable in various cosmetic formulations may also be added to the antimicrobial composition as long as they do not adversely affect the overall properties of the antimicrobial composition.

If desired, the antimicrobial composition of the invention may include a perfume to provide a pleasing scent or a dye to provide a characteristic color.

In another embodiment of the invention, the antimicrobial composition comprises:

(a) PCMX;
(b) a block polymer; and
(c) ethyl alcohol.

In this embodiment, the antimicrobial composition provides maximum antimicrobial properties without compensation for mildness characteristics. This embodiment recognizes the unique combination of a specific antimicrobial agent with a specific nonionic and anionic surfactant.

The antimicrobial compositions of the present invention are believed to be highly effective against common microorganisms such as *Staphylococcus aureus, Pseudomonas aeruginosa, Candida albicans* and *Escherichia coli*, among others as well. It is recognized, however, that the effectiveness of the antimicrobial composition depends upon the particular combination of materials, the concentration of ingredients used and the nature of the particular microorganism. Most importantly, the effectiveness of the antimicrobial composition depends on the combination and selection of the antimicrobial agent and the nonionic and anionic surfactants.

Generally, the composition may be in liquid form but may also be in the form of a gel or ointment.

Various other modifications will be apparent to and may be readily made by those skilled in the art without departing from the scope and spirit of the invention.

The examples are not limited to any specific embodiment of the invention, but are only exemplary.

EXAMPLE I

FORMATION OF AN ANTIMICROBIAL COMPOSITION

An antimicrobial composition was made by mixing in a suitably sized vessel, for a sufficient amount of time to insure homogeneity, to form a solution A, the following ingredients:

| INGREDIENTS | WT PERCENT |
|---|---|
| Polyoxyethylene polyoxypropylene condensates | 3.0 |
| Sulfated nonylphenol ethoxylates | 8.0 |
| Propylene glycol | 6.0 |
| MAX PEG-75 Lanolin MQH | 4.0 |
| Ammonium lauryl sulfosuccinate | 8.0 |
| Aloe Vera | 0.2 |
| Isopropyl Palmitate Lanolin Oil | 1.0 |
| Parachlorometaxylenol | 3.2 |

In a separate vessel, a solution B of 0.5% of hydroxylpropyl methylcellulose, 65.3% of deionized water and 0.5% of ethylenediamine tetraacetic acid (EDTA) was mixed for 60 minutes until all of the hydroxylpropyl methylcellulose was dissolved and no evidence of granulation remained.

Solutions A and B were then mixed together thoroughly for 60 minutes and during the mixing, 0.30% of fragrance was added. Then approximately 0.5% of 6N hydrochloric acid and 0.5% of 5N sodium hydroxide were added to adjust the pH to about 4.5.

The solution was then left without agitation for approximately 12 hours until the solution became clear.

EXAMPLE II

FORMATION OF AN ANTIMICROBIAL COMPOSITION

An antimicrobial composition was made by mixing in a suitably sized vessel for a sufficient amount of time to insure homogeneity, to form a solution A, the following ingredients:

| INGREDIENTS | WT PERCENT |
|---|---|
| Polyoxyethylene polyoxypropylene condensates | 3.0 |
| Sulfated nonylphenol ethoxylates | 8.0 |
| Propylene glycol | 6.0 |
| MAX PEG-75 Lanolin MQH | 4.0 |
| Ammonium lauryl sulfosuccinate | 8.0 |
| Aloe Vera | 0.2 |
| Isopropyl Palmitate Lanolin Oil | 1.0 |
| Parachlorometaxylenol | 3.2 |

In a separate vessel a solution B of 0.5% of hydroxylpropyl methylcellulose and 65.8% of deionized water was mixed for approximately 60 minutes until all of the hydroxylpropyl methylcellulose was dissolved and no evidence of granulation remained.

Solutions A and B were then mixed together thoroughly for 60 minutes and during the mixing, 0.30% of fragrance was added. Then approximately 0.5% of 6N hydrochloric acid and 0.5% of 5N sodium hydroxide were added to adjust the pH to about 4.5.

The solution was then left without agitation for approximately 12 hours until the solution became clear.

EXAMPLE II

COMPARATIVE ANALYSIS OF RELATED ANTIMICROBIAL COMPOSITION TO THE ANTIMICROBIAL COMPOSITIONS OF THE PRESENT INVENTION

Testing was conducted to compare the efficacy of the antimicrobial composition of U.S. Pat. No. 4,632,772 to Garabedian et al. to the antimicrobial composition of the present invention.

Samples from Examples I and II above, designated as A and B respectively, were compared to the commercially available antimicrobial composition of Garabedian et al., ULTRADEX® (trademark of Dexide, Inc., Fortworth, Tex.) which contains 3.0% PCMX, designated as C in the following table.

Full strength compositions of A, B and C were serially diluted 1:10 and 1:100. Each dilution was challenged with 0.1 ml of inoculum containing the number of colony forming units (CFU) of the following organisms, *Staphylococcus aureus*, *Pseudomonas aeruginosa*, *Candida albicans* and *Escherichia coli*. The results are reported in Table II below showing the kill times in minutes.

TABLE II

| ORGANISM | DILUTIONS | KILL TIMES (Minutes) | | |
|---|---|---|---|---|
| | | A | B | C |
| 1. *Staphylococcus aureus* | Full | 5 minute | 1 minute | 1 minute |
| $4.0 \times 10^6$ CFU | 1:10 | 1 minute | 1 minute | Positive |
| | 1:100 | Positive | 5 minute | Positive |
| 2. *Pseudomonas aeruginosa* | Full | 1 minute | 1 minute | 1 minute |
| $1.6 \times 10^7$ CFU | 1:10 | 1 minute | 5 minute | Positive |
| | 1:100 | Positive | Positive | Positive |
| 3. *Candida albicans* | Full | 1 minute | 1 minute | 1 minute |
| $1.9 \times 10^5$ CFU | 1:10 | 5 minute | 5 minute | 1 minute |
| | 1:100 | Positive | Positive | Positive |
| 4. *Escherichia coli* | Full | 1 minute | 1 minute | 1 minute |
| $3.2 \times 10^7$ CFU | 1:10 | 1 minute | 5 minute | Positive |
| | 1:100 | Positive | Positive | Positive |

Positive - colonies observed, total kill not achieved.

This test demonstrated that the antimicrobial compositions A and B of the present invention were significantly more effective than the composition C disclosed in Garabedian et al. In particular, composition B, without ethylenediamine tetraacetic acid (EDTA) provides a more effective composition than A.

Since *Staphylococcus aureus* is a commonly found organism on skin and is often difficult to kill completely, the formulation of the present invention as illustrated in Table II above, represents a marked and unexpected improvement over prior art cleansing formulations.

Since surgical scrub products in use are diluted three-to-four times, it is important that a product must remain bactericidal under those conditions. It is clearly evident that the present invention as illustrated in Table II above effectively remains bactericidal at least up to a dilution of ten times its volume.

What is claimed is:

1. An antimicrobial composition comprising:

(a) parachlorometaxylenol in an amount from 1.5 to about 3.5 weight percent of the total composition;

(b) poly(oxypropylene) poly-(oxyethylene) in an amount from 1.0 to 6.0 weight percent of the total composition;

(c) an ammonium salt of sulfated nonylphenoxypoly(ethyleneoxy) ethanol in an amount from 2.0 to 12.0 weight percent of the total composition;

(d) ammonium lauryl sulfosuccinate in an amount from about 2.0 to about 12.0 weight percent of the total composition;

(e) lanolin in an amount from about 5.0 to about 15.0 weight percent of the total composition;

(f) cellulose, 2-hydroxyethyl ether in an amount from about 0.1 to about 1.0 weight percent of the total composition;

(g) an acid to adjust the pH in the range of from about 4 to about 6; and (h) the balance water.

* * * * *